United States Patent

Tsuboi et al.

Patent Number: 5,308,855

Date of Patent: May 3, 1994

[54] GUANIDINE DERIVATIVES

[75] Inventors: Shin-ichi Tsuboi; Koichi Moriya, both of Tochigi; Yumi Hattori; Shinzaburo Sone, both of Ibaragi; Katsuhiko Shibuya, Tochigi, all of Japan

[73] Assignee: Nihon Bayer Agrochem, Tokyo, Japan

[21] Appl. No.: 987,513

[22] Filed: Dec. 7, 1992

[30] Foreign Application Priority Data

Dec. 19, 1991 [JP] Japan ................... 3-354053

[51] Int. Cl.$^5$ ................... A61K 31/44; C07D 401/06
[52] U.S. Cl. ................... 514/341; 514/256; 514/365; 546/278; 544/333; 548/202
[58] Field of Search ................... 546/278; 514/341

[56] References Cited

U.S. PATENT DOCUMENTS 4,806,553  2/1989  Shiokawa ................... 514/332

FOREIGN PATENT DOCUMENTS 0254859  2/1988  European Pat. Off. .
0383091  8/1990  European Pat. Off. .
0425978  5/1991  European Pat. Off. .

Primary Examiner—Jane T. Fan
Attorney, Agent, or Firm—Sprung, Horn, Kramer & Woods

[57] ABSTRACT

Insecticidal guanidine derivatives of the formula $$Z-CH(R^1)-N(\text{-}(CH_2)_n\text{-})N-C(=N-Y)-N(R^4)(R^5) \quad \text{with } R^2, R^3 \text{ substituents} \tag{I}$$

wherein
Z represents an optionally substituted five- or six-membered ring containing at least one ring hetero atom selected from the group consisting of oxygen, sulfur and nitrogen,
$R^1$ represents hydrogen atoms or a $C_{1-4}$ alkyl group,
$R^2$ and $R^3$ each independently represents hydrogen, $C_{1-4}$ alkyl, $C_{1-4}$ haloalkyl or optionally substituted phenyl,
$R^4$ and $R^5$ each independently represents hydrogen, $C_{1-4}$ alkyl, $C_{3-4}$ alkenyl, $C_{3-4}$ alkynyl, optionally substituted benzyl or a group of the formula Z-C($R^1$)H-,
n represents the integer 2 or 3, and
Y represents nitro or cyano.

9 Claims, No Drawings

GUANIDINE DERIVATIVES

The present invention relates to novel guanidine derivatives, to a process for their preparation, and to their use as insecticides.

It has already been disclosed that a certain group of guanidine derivatives is useful as insecticides (see Japanese Laid-open patent application No. 10762/1988).

There have now been found novel guanidine derivatives of the formula (I)

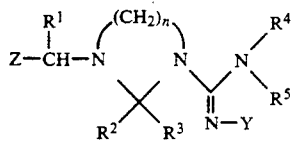

wherein

Z represents an optionally substituted five- or six-membered ring containing at least one ring hetero atom selected from the group consisting of oxygen, sulfur and nitrogen, $R^1$ represents hydrogen atoms or a $C_{1-4}$ alkyl group, $R^2$ and $R^3$ each independently represents hydrogen, $C_{1-4}$ alkyl, $C_{1-4}$ haloalkyl or optionally substituted phenyl, $R^4$ and $R^5$ each independently represents hydrogen, $C_{1-4}$ alkyl, $C_{3-4}$ alkenyl, $C_{3-4}$ alkynyl, optionally substituted benzyl or a group of the formula Z-$C(R^1)H$-, n represents the integer 2 or 3, and Y represents nitro or cyano.

The guanidine derivatives of the formula (I) are obtained when compounds of the formula

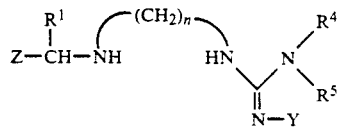

are reacted with compounds of the formula

in the presence of inert solvents, if appropriate in the presence of catalysts.

The novel guanidine derivatives of the formula (I) exhibit powerful insecticidal properties.

Surprisingly, the guanidine derivatives according to the invention exhibit a substantially greater insecticidal action than those known from the above-mentioned Japanese Laid-open patent application.

Among the guanidine derivatives according to the invention, of the formula (I), preferred compounds are those in which Z represents pyridyl, chloropyridyl, or a thiazolyl radical which may be substituted, $R^1$ represents hydrogen or methyl, $R^2$ and $R^3$ each independently represents hydrogen, methyl, trichloromethyl, phenyl or chlorophenyl, $R^4$ and $R^5$ each independently represents hydrogen, methyl, allyl, propargyl, benzyl, chlorobenzyl or 2-chloro-5-pyridylmethyl, n represents the integer 2 or 3, and Y represents nitro or cyano.

Very particularly preferred guanidine derivative of the formula (I) are those in which Z represents 2-chloro-5-pyridyl or 2-chloro-5-thiazolyl, $R^1$, $R^2$, $R^3$, $R^4$ and $R^5$ each independently represents hydrogen or methyl, n represents the integer 2 or 3, and Y represents nitro.

As specific examples of compounds of formula (I) according to the invention there may be mentioned:
1-(6-chloro-3-pyridylmethyl)-3-{1-(nitroimino)-aminomethyl}-imidazolidine,
1-(5-chloro-5-thiazolylmethyl)-3-{1-(nitroimino)-aminomethyl}-imidazolidine, 1-(6-chloro-3-pyridylmethyl)-3-methyl-{1-(nitroimino)-aminomethyl}-imidazolidine, and
1-(6-chloro-3-pyridylmethyl)-3-{1-(cyanoimino)-aminomethyl}-imidazolidine.

If, for example, 1-{2-(6-chloro-3-pyridylmethylamino) ethyl}-2-nitroguanidine and formaldehyde are used as starting materials, the course of the reaction can be represented by the following equation:

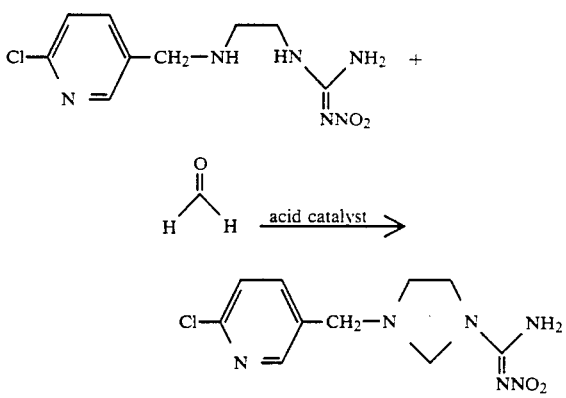

The starting material of the formula (II) can be obtained by reacting amines disclosed in Japanese Laid-Open Patent application No. 267561/1986 and 46480/1987 with isothioureas, according to the method disclosed in J.A.C.S., vol. 76, 1877-1879, 1954.

As specific examples of compounds of formula (II) there may be mentioned:
1-{2-(6-chloro-3-pyridylmethylamino)ethyl}-2-nitroguanidine,
1-{2-(2-chloro-5-thiazolylamino)ethyl}-2-nitroguanidine,
1-{2-(6-chloro-3-pyridylmethylamino)ethyl}-3-methyl-2-nitroguanidine,
1-{2-(6-chloro-3-pyridylmethylamino)ethyl}-2-cyanoguanidine, and
1-{2-(6-chloro-3-pyridylmethylamino)propyl}-2-nitroguanidine, The compounds of the formula (III) are well known and, as specific examples, there may be mentioned: formaldehyde, acetaldehyde, propionaldehyde, chloral, benzaldehyde, p-chlorobenzaldehyde and acetone.

In carrying out the process, use may be made, as a suitable diluent, of any inert solvent.

Examples of such diluents are water; aliphatic, cycloaliphatic and aromatic, optionally chlorinated, hydrocarbons such as pentane, hexane, cyclohexane, petroleum ether, ligroin, benzene, toluene, xylene, dichloromethane, chloroform, carbon tetrachloride, ethylene chloride, chlorobenzene, dichlorobenzene, and the like; ethers such as diethyl ether, methyl ethyl ether, di-isopropyl ether, di-butyl ether, propylene oxide, dimethoxyethane (DME), dioxane, tetrahydrofurane (THF) and the like; nitriles such as acetonitoride, propionitrile, acrylonitrile, and the like; alcohols such as methanol, ethanol, iso-propanol, butanol, ethylene glycol and the like; esters such as ethyl acetate, amyl acetate, and the like; acid amides such as dimethyl formamide (DMF), diethyl acetamide (DMA), N-methylpyrrolidone, 1,3-dimethyl-2-imidazolidinone, hexamethylphosphoric triamide (HMPA) and the like; sulfones and sulfoxides such as dimethyl sulfoxide (DMSO), sulfolane and the like; and, bases, for example, such as pyridine.

The reaction is carried out in the presence of catalysts such as, for example, acetic acid, hydrochloric acid, hydrobromic acid, p-toluene sulfonic acid and trifluoroacetic acid.

The reaction temperature can be varied within a substantially wide range. In general, the reaction is carried out at a temperature of from about −20° C. to about 120° C., preferably from 10° C. to about 60° C.

Further, the reaction is carried out under normal pressure, although it is also possible to employ a higher or reduced pressure.

In carrying out the process about 1.0 to 1.2 mols of compound (III) are employed per mol of compound (II), in the presence of inert solvents such as water and a catalytic amount of hydrochloric acid, for example, to obtain the desired compounds of the formula (I).

The active compounds of the formula (I) are well tolerated by plants, have a favorable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example, *Oniscus Asellus, Armadillidium vulgare* and *Porcellio scaber;* from the class of the Diplopoda, for example, *Blaniulus guttulatus;* from the class of the Chilopoda, for example, *Geophilus carpophagus* and Scutigera spec.;

from the class of the Symphyla, for example, *Scuti gerella immaculata;* from the order of the Thysanura, for example, *Lepisma saccharina;* from the order of the Collembola, for example, *Onychiurus armatus;* from the order of the Orthoptera; for example, *Blatta orientalis, Periplaneta americana, Leucophaea maderae, Blattela germanica, Acheta domesticus,* Gryllotalpa spp., *Locusta migrato ria migratorioides, Melanoplus differentialis* and *Schistocerca gregaria;* from the order of the Dermaptera, for example, *Forficula auticularia;* from the order of the Isoptera, for example, Reticulitermes spp.;

from the order of the Anoplura, for example, *Phylloxera vastatrix,* Pemphigus spp., *Pediculus humanus corporis,* Haematopinus spp. and Linognathus spp.;

from the order of the Mallophaga, for example, Trichodectes spp. and Damalinea spp.;

from the order of the Thysanoptera, for example, *Hercinothrips femoralis* and *Thrips tabaci,* from the order of the Heteroptera, for example, Eurygaster spp., *Dysdercus intermedius, Piesma guadrata, Cimex lectularius, Rhodnius prolixus* and Triatoma spp.;

from the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Dorallis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticepts, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistic citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon chochleariae,* Diabrotica spp., *Psylliodes chrysocephala, Epilachna varivestis,* Atomaria spp., *Oryzaephilus surinamensis,* Anthonomus spp., Sitophilus spp., *Otiorr hynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera for example, Diprion spp., Hoplocampa spp., Lasius spp., *Monomorium pharaonis* and Vespa spp.;

from the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

The active compounds can be converted into the customary formulations, such as solutions, emulsions, wettable powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products.

Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergistic agent are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The preparation and use of the active compounds according to the invention can be seen from the following examples.

EXAMPLE 1

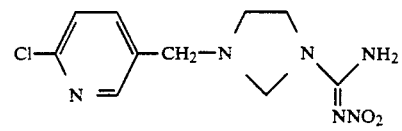

A mixture consisting of 1-{2-(6-chloro-3-pyridylmethylamino)ethyl}-2-nitroguanidine (1 g), a 37% aqueous solution of formalin (0.35 g), catalytic amount of hydrochloric acid, and water (20 ml) was stirred at 50° C. for one hour. After cooling, the solvent was removed from the reaction mixture under reduced pressure, leaving crystals that were then washed with chloroform to obtain the 1-(6-chloro-3-pyridylmethyl)-3-{1-(nitroimino)-aminomethyl}-imidazolidine. mp 170°–174° C.

The product of Example 1 along with other compounds similarly produced are shown in the following Table:

TABLE $$Z-\underset{R^2}{\underset{|}{C}H}-N-\underset{R^3}{\underset{|}{C}}\begin{smallmatrix}(CH_2)_n\\|\\N\\|\\N-Y\end{smallmatrix}\begin{smallmatrix}R^4\\ \diagup\\N\\ \diagdown\\R^5\end{smallmatrix}$$

| Comp. No. | Z | $R^1$ | $R^2$ | $R^3$ | $R^4$ | $R^5$ | n | Y | Melting point (°C.) |
|---|---|---|---|---|---|---|---|---|---|
| 1 | 6-Cl-pyridin-3-yl 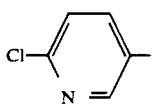 | H | H | H | H | H | 2 | $NO_2$ | 170–174 |
| 2 | 6-Cl-pyridin-3-yl 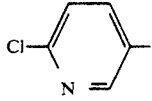 | H | H | H | H | H | 3 | $NO_2$ | |
| 3 | 6-Cl-pyridin-3-yl 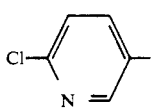 | H | $CH_3$ | H | H | H | 2 | $NO_2$ | |
| 4 | 6-Cl-pyridin-3-yl 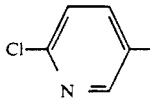 | H | $CH_3$ | $CH_3$ | H | H | 2 | $NO_2$ | |
| 5 | 6-Cl-pyridin-3-yl 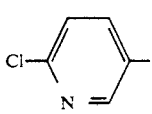 | H | H | H | $CH_3$ | H | 2 | $NO_2$ | |
| 6 | 6-Cl-pyridin-3-yl 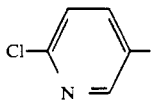 | H | H | H | $CH_3$ | $CH_3$ | 3 | $NO_2$ | |
| 7 | 6-Cl-pyridin-3-yl 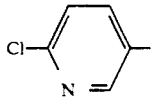 | $CH_3$ | H | H | H | H | 3 | $NO_2$ | |
| 8 | 6-Cl-pyridin-3-yl 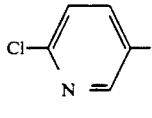 | H | $CH_3$ | H | $-CH_2$-(6-Cl-pyridin-3-yl) 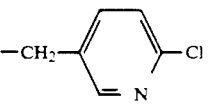 | H | 2 | $NO_2$ | |
| 9 | 6-Cl-pyridin-3-yl 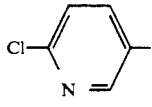 | H | 4-Cl-phenyl 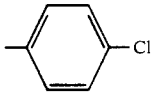 | H | H | H | 2 | $NO_2$ | |
| 10 | 6-Cl-pyridin-3-yl 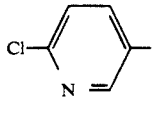 | H | H | H | $-CH_2-CH=CH_2$ | H | 2 | $NO_2$ | |
| 11 | 6-Cl-pyridin-3-yl 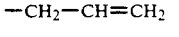 | H | H | H | $-CH_2-CH=CH_2$ | H | 3 | $NO_2$ | |

TABLE-continued $$Z-\underset{R^2}{\underset{|}{C}}H-N\underset{R^3}{\overset{R^1}{\diagdown}}\underset{N-Y}{\overset{(CH_2)_n}{C}}\underset{R^5}{\overset{R^4}{\diagup}}$$

| Comp. No. | Z | $R^1$ | $R^2$ | $R^3$ | $R^4$ | $R^5$ | n | Y | Melting point (°C.) |
|---|---|---|---|---|---|---|---|---|---|
| 12 | 2-chloro-5-thiazolyl | H | H | H | H | H | 2 | $NO_2$ | |
| 13 | 2-chloro-5-thiazolyl | H | H | H | $-CH_2-$(6-chloro-3-pyridyl) | H | 2 | $NO_2$ | |
| 14 | 6-chloro-3-pyridyl | H | $CCl_3$ | H | H | H | 2 | $NO_2$ | |
| 15 | 2-chloro-5-thiazolyl | H | H | H | H | H | 2 | CN | |
| 16 | 6-chloro-3-pyridyl | H | H | H | H | H | 2 | CN | |
| 17 | 4-methyl-1,2,5-thiadiazol-3-yl | H | $CCl_2CH_3$ | H | H | H | 2 | $NO_2$ | |
| 18 | 6-methyl-3-pyridyl | H | $CF_3$ | $CH_3$ | H | H | 2 | CN | |
| 19 | 3-bromo-5-isoxazolyl | H | H | H | H | H | 2 | $NO_2$ | |
| 20 | 1-methyl-pyrazol-4-yl | H | $CF_2CF_2CF_3$ | H | H | H | 2 | $NO_2$ | |
| 21 | 2-methyl-5-pyrimidinyl | H | H | H | H | H | 2 | $NO_2$ | |

EXAMPLE 2 (SYNTHESIS OF STARTING MATERIAL)

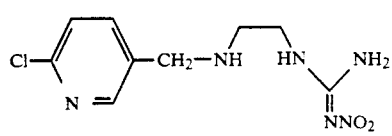

A mixture consisting of N-(6-chloro-3-pyridyl-methyl) ethylenediamine (3.7 g), 3-nitoro-2-methylisothiourea (2.7 g) and ethanol (20 ml) was stirred at 30° C. until methylmercaptan ceased to be generated therefrom. After cooling, the separated crystals were taken out under filtration, to obtain the desired 1-{2-(6-chloro-3-pyridyl-methylamino)ethyl}-2-nitroguanidine. mp 119°–122° C.

BIOTEST EXAMPLE A: CARRIED OUT AGAINST NEPHOTETTIX CINCTICEPS (GREEN RICE LEAFHOPPER) EXHIBITING RESISTANCE TO ORGANOPHOSPHORUS AND CARBAMATE SERIES INSECTICIDES

Preparation of test formulation solvent: 3 parts by weight of xylene

Emulsifier: 1 part by weight of polyoxyethylenealkyl-phenyl-ether

To prepare suitable formulations of the active compounds, 1 part by weight of each of the active compounds was mixed with the above-mentioned amount of the solvent containing the above-mentioned amount of the emulsifier, and the mixture was diluted with water to the predetermined concentration.

Test Method

Use was made of a plurality of pots each having a diameter of 12 cm in which were planted rice plant seedlings each having a height of about 10 cm. Onto each of the potted rice-plant seedlings there were sprayed 10 ml of an aqueous solution of the formulation. After the solution dried, each pot was covered with a metallic net having a diameter of 7 cm and height of 14 cm, into which there were released 30 female adults of Nephotettix cincticeps exhibiting resistance to organophosphorus and carbamate series insecticides, and then each pot was placed in a constant temperature chamber. After two days, the number of killed insects was determined to obtain the insect mortality.

BIOTEST EXAMPLE B: CARRIED OUT AGAINST PLANTHOPPERS EXHIBITING RESISTANCE TO ORGANOPHOSPHORUS AND CARBAMATE INSECTICIDES

Test Method

Use was made of a plurality of pots each having a diameter of 12 cm in which were planted rice plant seedlings each having a height of about 10 cm. Onto each of the potted rice-plant seedlings there were sprayed 10 ml of an aqueous solution of the formulation of Example A. After the solution dried, each pot was covered with a metallic net having a diameter of 7 cm and height of 14 cm, into which there were released 30 female adults of brown planthoppers (Nilaparvata lugens) exhibiting resistance to organophosphorus and carbamate-series insecticides, and then each pot was placed in a constant temperature chamber. After two days, the number of killed insects was determined to obtain the insect mortality.

In similar manner, mortality was determined each on Sezirounka (white-backed planthopper, *Sogatella furcifera*) and Himetobiunka (smaller blown planthopper, *Laodelphax striatellus*) having resistance to organophosphoric pesticides.

In the above-mentioned Test Examples A and B, use was made of the compound 1 in Table 1, with 100% control on each of the noxious insects at a dosage of 200 ppm.

It will be understood that the specification and examples are illustrative but not limitative of the present invention and that other embodiments within the spirit and scope of the invention will suggest themselves to those skilled in the art.

We claim:

1. A guanidine compound of the formula

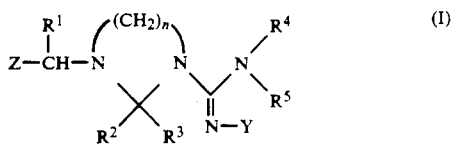

wherein
Z represents an optionally chlorine substituted pyridyl group,
$R^1$ represents hydrogen atoms or a $C_{1-4}$ alkyl group,
$R^2$ and $R^3$ each independently represents hydrogen, $C_{1-4}$ alkyl, $C_{1-4}$ haloalkyl or optionally chlorine substituted phenyl,
$R^4$ and $R^5$ each independently represents hydrogen, $C_{1-4}$ alkyl, $C_{3-4}$ alkenyl, $C_{3-4}$ alkynyl, or optionally chlorine substituted benzyl,
n represents the integer 2, and
Y represents nitro or cyano.

2. A compound according to claim 1, wherein
Z represents pyridyl or chloropyridyl,
$R^1$ represents hydrogen or methyl,
$R^2$ and $R^3$ each independently represents hydrogen, methyl, trichloromethyl, phenyl or chlorophenyl,
$R^4$ and $R^5$ each independently represents hydrogen, methyl, allyl, propargyl, benzyl, or chlorobenzyl.

3. A compound according to claim 1, wherein
Z represents 2-chloro-5-pyridyl,
$R^1$, $R^2$, $R^3$, $R^4$ and $R^5$ each independently represents hydrogen or methyl, and
Y represents nitro.

4. A compound according to claim 1, wherein such compound is 1-(6-chloro-3-pyridylmethyl)-3-{1-(nitroimino)-aminomethyl}-imidazolidine.

5. A compound according to claim 1, wherein such compound is 1-(6-chloro-3-pyridylmethyl)-3-methyl-{1-(nitroimino)-aminomethyl}-imidazolidine.

6. A compound according to claim 1, wherein such compound is 1-(6-chloro-3-pyridylmethyl)-3-{1-(cyanoimino)-aminomethyl}-imidazolidine.

7. An insecticidal composition comprising an insecticidally effective amount of a compound according to claim 1 and a diluent.

8. A method of combating insects which comprises applying to such insects or to an insect habitat an insecticidally effective amount of a compound according to claim 1.

9. The method according to claim 8, wherein such compound is
1-(6-chloro-3-pyridylmethyl)-3-{1-(nitroimino)-aminomethyl}-imidazolidine.
1-(6-chloro-3-pyridylmethyl)-3-methyl-{1-(nitroimino)-aminomethyl}-imidazolidine or
1-(6-chloro-3-pyridylmethyl)-3-{1-(cyanoimino)-aminomethyl}-imidazolidine.

* * * * *